United States Patent [19]

Hardy et al.

[11] 4,304,639

[45] Dec. 8, 1981

[54] PROCESS FOR THE PURIFICATION OF OLEFINE OXIDES

[75] Inventors: Nicolas Hardy; Teddy Durieux, both of Jemeppe-sur-Sambre, Belgium

[73] Assignee: Propylox (Societe Anonyme), Brussels, Belgium

[21] Appl. No.: 137,827

[22] Filed: Apr. 7, 1980

[30] Foreign Application Priority Data

Apr. 6, 1979 [FR] France ................. 79 09121

[51] Int. Cl.³ .................... B01D 3/34; C07D 301/32
[52] U.S. Cl. ........................... 203/33; 203/36; 203/37; 203/96; 203/98; 203/DIG. 19; 203/53; 260/348.37
[58] Field of Search ................. 203/95–97, 203/DIG. 19, 76, 83, 79, 85, 99, 98, 33, 36, 37, 39, 53; 260/348.37

[56] References Cited

U.S. PATENT DOCUMENTS

| | | | |
|---|---|---|---|
| 2,550,847 | 5/1951 | Mitchell et al. | 260/348.37 |
| 3,398,062 | 8/1968 | Tsao | 260/348.37 |
| 3,418,338 | 12/1968 | Gilman et al. | 260/348.37 |
| 3,477,919 | 11/1969 | Lichtenwalter et al. | 260/348.37 |
| 3,507,755 | 4/1970 | Bitners et al. | 203/98 |
| 3,531,376 | 9/1970 | Minoda et al. | 203/98 |
| 3,738,915 | 6/1973 | DiFiore et al. | 203/98 |
| 3,860,495 | 1/1975 | Borrel et al. | 203/98 |
| 4,134,797 | 1/1979 | Ozero | 203/DIG. 19 |
| 4,140,588 | 2/1979 | Schmidt | 260/348.37 |

FOREIGN PATENT DOCUMENTS 2317296 2/1977 France.
47-18812 9/1972 Japan.

*Primary Examiner*—Wilbur L. Bascomb, Jr.
*Attorney, Agent, or Firm*—Spencer & Kaye

[57] ABSTRACT

A process for the purification of olefine oxides by subjecting a mixture containing the olefine oxides to distillation in a distillation column in the presence of a small amount of water in order to obtain olefine oxide as the distillate. A fraction of the down-flow liquid is withdrawn from the column and the withdrawn fraction is subjected to decantation, so as to separate off an aqueous phase which is discarded, and an organic phase. The organic phase is returned to the column at a point located below the withdrawal point.

10 Claims, 2 Drawing Figures

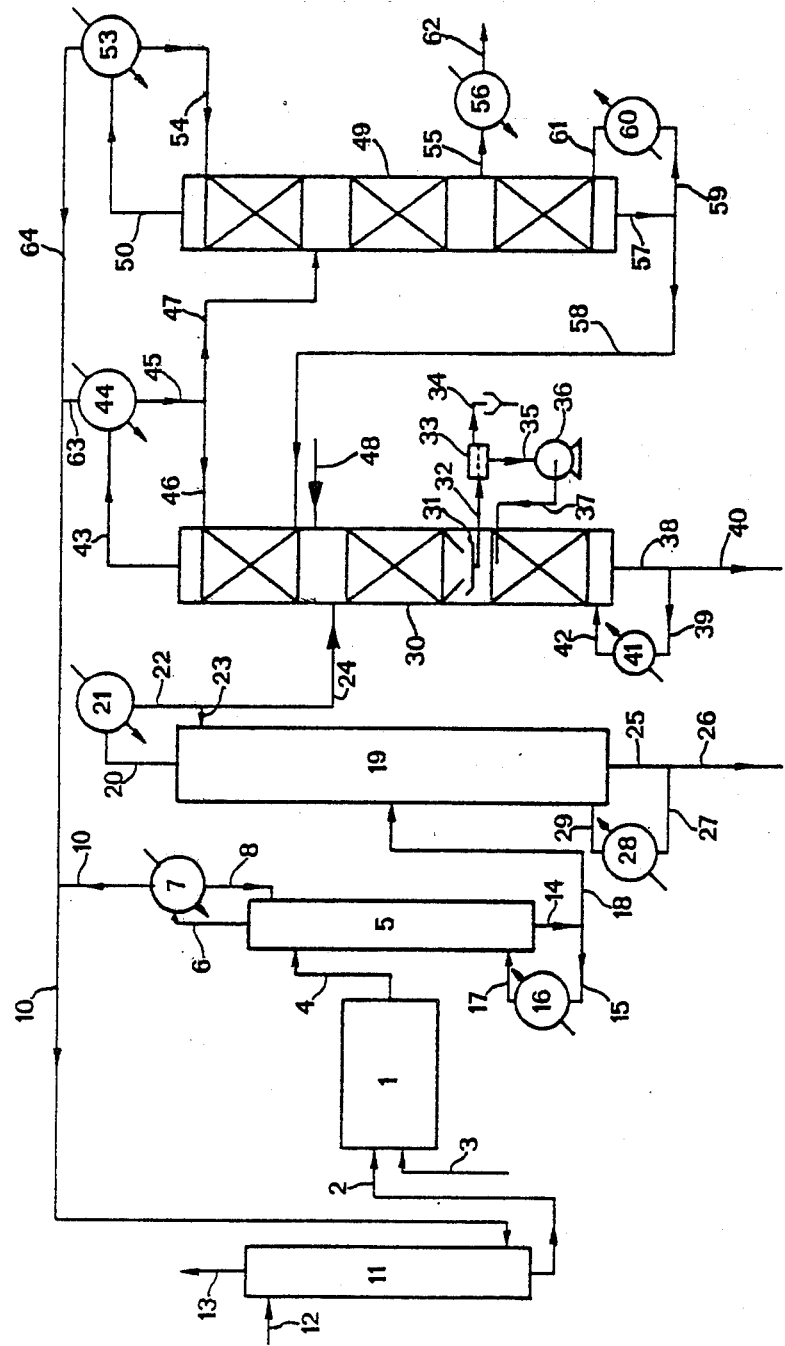

PROCESS FOR THE PURIFICATION OF OLEFINE OXIDES

BACKGROUND OF THE INVENTION

The present invention relates to a process for the purification of olefine oxides. More particularly, it relates to the purification of the olefine oxides obtained by epoxidising the corresponding olefines with peroxide compounds.

In the epoxidation of olefines with peroxide compounds, such as hydrogen peroxide or percarboxylic acids, olefine oxides containing various impurities, such as water, glycols, aldehydes, alcohols, unreacted olefine and the solvent which may have been used, are obtained at the outlet of the epoxidation reactor or after preliminary rectification. Some of these products, which prove troublesome when the olefine oxides are used, for example, as a monomer for the manufacture of polymers, are very difficult to remove by the conventional distillation techniques. Moreover, during the numerous distillation steps required for their removal, the formation of large amounts of by-products, such as esters and glycols, is observed.

Thus, in the manufacture of propylene oxide by epoxidising propylene with an organic solution of a peracid (Belgian Pat. No. 847,664, filed on Oct. 27, 1976 in the name of Bayer AG and Degussa), propylene glycol is formed during the steps for separating the reaction mixture into its various constituents.

In order to remove the esters present in propylene oxide, it has been proposed (Japanese Patent Application No. 47/18,812, filed on Feb. 16, 1971 in the name of Mitsubishi Chem. Ind. LTD.) to treat the propylene oxide in a distillation column in the presence of an aqueous solution of a saponifying agent. However, this technique exhibits the disadvantage that it causes considerable corrosion in the still of the distillation column.

SUMMARY OF THE INVENTION

The object of the present invention is to provide a process for the purification of olefine oxides, which makes it possible to overcome these disadvantages and, in particular, to purify the olefine oxides efficiently while at the same time avoiding the formation of secondary products and corrosion.

Moreover, the process according to the invention is particularly easy to carry out. It requires a small number of distillation columns while at the same time making it possible to separate off the aldehydes efficiently.

For this purpose, the invention relates to a process for the purification of olefine oxides by subjecting a mixture containing the olefine oxide to column distillation, in the presence of a small amount of water, so as to obtain the olefine oxide as the distillate. In accordance with this process, a fraction of the down-flow liquid is withdrawn from the column and, the withdrawn fraction is subjected to decantation, with or without prior cooling, so as to separate off an aqueous phase, which is discarded, and an organic phase. The organic phase is returned to the column at a point located below the withdrawal point.

BRIEF DESCRIPTION OF THE DRAWINGS

FIGS. 1 and 2 are schematic diagrams of apparatus which can be used for practicing the process of the present invention.

DETAILED DESCRIPTION OF THE INVENTION

Figure 1:
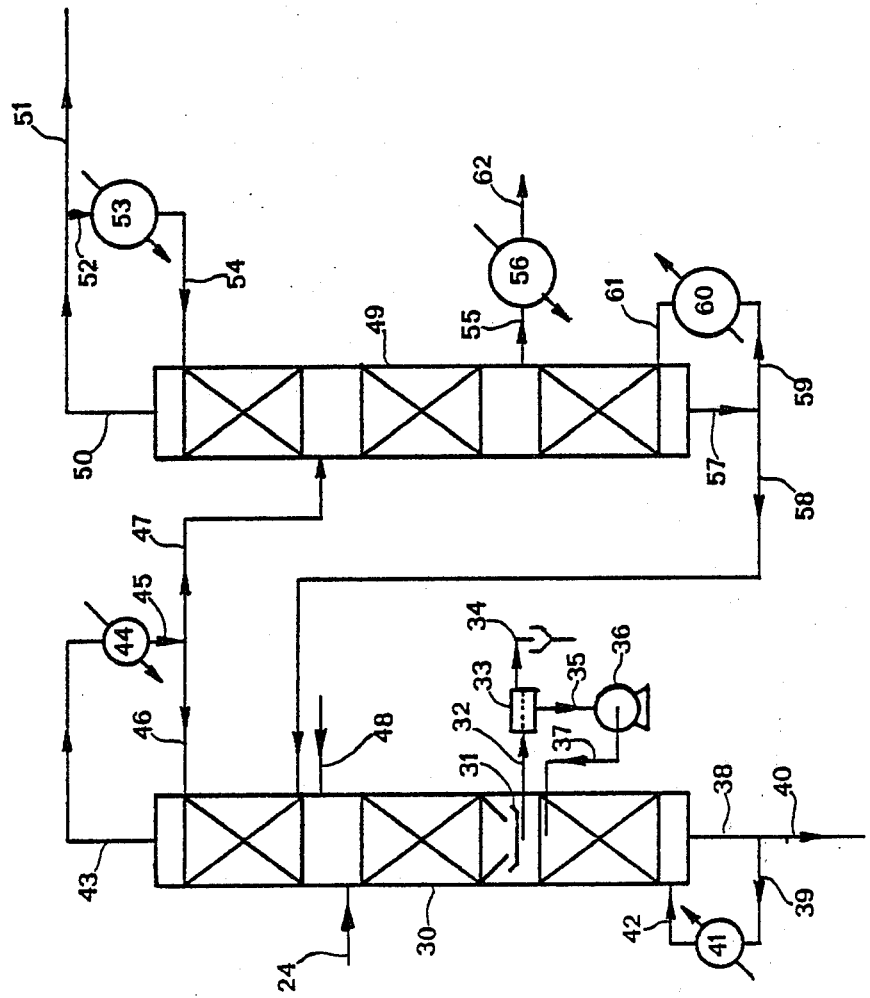

In the process of the present invention, the relative amount of the down-flow liquid withdrawn is not in itself critical. Generally, it is adjusted in accordance with the amount of water present in the propylene oxide. In general, arrangements are made to withdraw at least 10% of the down-flow liquid.

The down-flow liquid can be withdrawn at any point on the distillation column. In general, the withdrawal point is located below the point of introduction of the mixture containing the olefine oxide to be purified. It is preferably chosen so as to prevent phase demixing in the distillation column beyond the location of the withdrawal. Goods results have been obtained when the withdrawal point is located between the point of introduction of the mixture containing the olefine to be purified and the lower tenth of the column.

The withdrawal can be carried out in accordance with various techniques. It is recommended that care be taken so that the withdrawal does not hinder the rising of the hot vapors in the column. One procedure, which has given good results, consists in arranging, in the column, a plate having the shape of a very flared funnel, which allows the hot vapours to pass at the side, collects the down-flow liquid and communicates, via a pipe, with a decanter/separator which can itself be located inside or outside the distillation column. Various types of decanter/separator devices which are in themselves known can be used for this purpose.

The organic phase separated off after decantation of the withdrawn fraction can be returned to the distillation column at any point on the column which is near or below the withdrawal point. Good results have been obtained when the organic phase is returned to the zone located directly below the withdrawal point.

The process according to the invention can be carried out continuously or semi-continuously. Good results have been obtained by continuously collecting a fraction of the down-flow liquid, by continuously subjecting it to decantation and separation, and by continuously returning the organic phase to the distillation column.

The water present in the distillation column can originate from various sources. It can be the water present as an impurity in the olefine oxide. It can also be added to the distillation column intentionally. Finally, it can also orginate from both these sources simultaneously. The latter solution has proved advantageous.

The total amount of water entering the distillation column is generally not more than 20% by weight of the mixture to be distilled, entering the column. Higher proportions of water are not favourable because they cause secondary hydrolysis reactions. Good results have been obtained when the weight ratio of the water to the mixture to be distilled, feeding the column, does not exceed 10%. Furthermore, in order to achieve adequate extraction of certain impurities, it is preferable to introduce, into the column, a total amount of water of at least 0.05% by weight of the mixture feeding the column. Good results have been obtained when this amount is at least 0.1% of that of the mixture.

The water intentionally introduced into the distillation column can be pure water or an aqueous solution. In general, an aqueous solution having a pH of more than 7 is preferably introduced into the column. These solutions can contain various types of compounds capable of imparting a basic character to the water. The nature of these compounds is arbitrary. In general, they are chosen from among alkali metal or alkaline earth metal hydroxides, carbonates and bicarbonates and mixtures thereof. Good results have been obtained with alkali metal hydroxides and more particularly sodium hydroxide.

These aqueous solutions can contain variable amounts of basic compounds. In general, in order to avoid the precipitation of certain salts in the aqueous phase subjected to decantation, aqueous solutions containing not more than 20% by weight of these basic compounds are preferably used. Good results have been obtained when the proportions thereof do not exceed 12% of the weight of the solution. Furthermore, it is generally preferred to use solutions containing at least 0.1% by weight of basic compounds. Good results have been obtained when these solutions contain at least 1% by weight of basic compounds.

The water or the aqueous solutions intentionally introduced into the column are introduced above the point of withdrawal of the down-flow liquid. In general, they are introduced into the column at a level which is identical to, or higher than, the level of introduction of the mixture containing the olefine oxide to be purified.

The aqueous solutions can be introduced at one or more points; the aqueous solution can also be added to the column feed.

The operating conditions of the distillation column in the process according to the invention are essentially chosen in accordance with the nature of the olefine oxide to be purified. Thus, very variable temperatures and pressures can be used.

The temperature is generally between 270° and 450° K. Higher temperatures are less advantageous because they involve a risk of secondary reactions. The pressure is adjusted in accordance with the temperature so as to maintain boiling. It is most frequently between 1 E+03 Pa and 5 E+06 Pa.

The process according to the invention can be used to purify various types of olefine oxides containing at least one epoxide bridge. The process is preferably applied to olefine oxides which contain groups

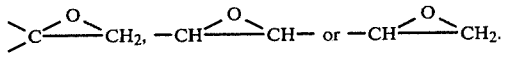

In general, the process is applied to alkene or cycloalkene oxides containing from 2 to 30 carbon atoms and most frequently to those containing from 2 to 20 carbon atoms in their molecule. The alkene or cycloalkene oxides to which the process is applicable can be unsubstituted or substituted by one or more substituents chosen from among alkyl groups generally containing from 1 to 4 carbon atoms, cycloalkyl groups, aryl groups or substituents containing hetero-atoms. Among the alkene or cycloalkene oxides which are unsubstituted or substituted solely by alkyl, cycloalkyl or aryl groups and to which the process according to the invention is applicable, the following may be mentioned more particularly: ethylene oxide, propylene oxide, methylpropene oxide, butene oxides, butadiene dioxide, pentene oxides, pentadiene dioxides and especially isoprene oxide, hexene oxides, hexadiene dioxides, diisobutylene oxide, octene oxides, nonene oxides, decene oxides, α-pinene oxide, p-menthene oxide, tri- and tetra-propylene oxides, tetradecene oxide, hexadecene oxide, octadecene oxide, dodecene oxide, eicosene oxide, styrene oxide, methylstyrene oxide, vinyltoluene oxide, vinylcyclohexane and -cyclohexene oxides, cyclohexene oxide, limonene oxide, divinylbenzene dioxide and stilbene oxides.

The alkene and cycloalkene oxides which can be used in the process of the invention can also be substituted by one or more substituents containing hetero-atoms, such as halogen atoms and more particularly chlorine, fluorine and bromine atoms, sulphonic or phosphoric acid groups and hydroxyl, alkoxy, carboxyl, acyl, alkoxycarbonyl, aryloxycarbonyl, acyloxy, acylamino, arylamido, alkylamido, imido or nitrilo groups.

The following may be mentioned more particularly as substituted olefines oxides which can be used: epichlorohydrin, epibromohydrin, methylepichlorohydrin, methylepibromohydrin, glycidol, methylglycidol, methoxyglycidol, ethoxyglycidol, the oxides of esters of acrylic acid, methacrylic acid and maleic acid with saturated or unsaturated alcohols, and also the oxides of esters of saturated carboxylic acids with unsaturated alcohols such as allyl alcohol and methallyl alcohol.

The process according to the invention is applied particularly successfully to the purification of propylene oxide, butene oxides, cyclohexene oxide, epichlorohydrin, styrene oxide, diepoxybutane and glycidol. Very good results have been obtained in the purification of mixtures based on propylene oxide.

Apart from the olefine oxide, the mixtures containing the olefine oxide subjected to purification contain impurities and various types of products, depending on the method used to manufacture the olefine oxide. These products are generally solvents and by-products from the epoxidising agent, together with unconverted reactants.

The nature of the solvents which may be present in the mixtures containing the olefine oxide can be very varied, depending on the method used to manufacture the olefine oxide. They generally consist of alcohols, carboxylic acid esters, ethers, halogenated hydrocarbons, unsubstituted hydrocarbons, hydrocarbons substituted by nitro groups, non-acidic esters of nitric acid, carbonic acid and phosphoric acid, nitriles, amides and mixtures thereof. These solvents are present in variable amounts in the mixture containing the olefine oxide to be purified. In general, the mixture to be purified can contain up to 90% by weight of solvent.

The mixture containing the olefine oxide can also contain unconverted olefine and residues from the epoxidising agent, such as, for example, water and carboxylic acids, and also various types of by-products including glycols, esters, aldehydes, alcohols and ketones. In general, the mixtures to be purified contain from 0.01 to 10% by weight of water and from 0.001 to 5% by weight of by-products. If the olefine oxide is obtained in accordance with a process involving peracid, they can additionally contain up to 25% by weight of the corresponding carboxylic acid.

If the mixture containing the olefine oxide has not been subjected to a prior separation of the olefine not converted during the epoxidation reaction, it can contain large amounts of olefine, which can reach and even exceed 10 times the amount of propylene oxide present.

The olefine oxide collected at the top of the column in the process according to the invention can be subjected to a subsequent distillation in order to remove the volatile products, such as, for example, the unconverted olefine and the volatile aldehydes, which could possibly still be present. In this case, the olefine oxide is advantageously sent into a further distillation column from which the volatile products, including the unconverted olefine which can be recovered if appropriate, are drawn off at the top. In the lower part of this column, the perfectly purified olefine oxide is collected, preferably in the gas phase, and the liquid collected at the bottom of this column is returned to the column operating according to the invention.

The impurities essentially removed by the process according to the invention are the water, the esters, the aldehydes and the glycols, and also the carboxylic acids, if appropriate in the form of salts in the case where the aqueous solution used for purification contains basic compounds.

The process according to the invention makes it possible to obtain purified olefine oxides which are suitable as a monomer for polymerisation. It can be applied particularly advantageously to the purification of olefine oxides obtained by the process involving peracids.

The process according to the invention can be carried out in apparatuses such as those shown schematically in FIGS. 1 and 2 of the attached drawings, which relate to particular practical embodiments.

In accordance with the process shown schematically in FIG. 1, a mixture containing the olefine oxide, small amounts of unconverted olefine, a solvent and impurities is introduced into the distillation column 30 via the line 24.

A plate 31 is arranged in the column 30 and makes it possible to collect part of the down-flow liquid from the column, this liquid being sent via the line 32 into a decanter 33, in which an aqueous phase is separated from an organic phase and drawn off via the line 34, the organic phase being drawn off via the line 35 and recycled by means of the pump 36 into the column 30 via the line 37.

Part of the liquid collected at the bottom of the column 30 via the line 38 is sent via the line 39 to the still 41, from which it is returned to the column 30 via the line 42. The other part is collected via the line 40. This liquid mainly comprises the solvent.

The aqueous solution is introduced into the column 30 via the line 48.

The vapours which contain the olefine oxide leave the column 30 via the line 43 and are condensed at 44, and part of the liquid leaving the condenser 44 via the line 45 is returned via the line 46 to the column, where it provides the reflux, the other part being sent via the line 47 into the column 49 for removal of the volatile components.

The purified olefine oxide is collected via the line 55 from one of the plates of the column, condensed at 56 and recovered at 62.

Part of the vapours collected at 50, which contain the olefine in particular, is recovered at 51 and the other part is sent via the line 52 into a condenser 53 in order to be recycled via the line 54 to the column 49, where it provides the reflux.

Part of the liquid collected at the bottom of the column 49 via the line 57 is sent via the line 59 to the still 60, from which it is returned to the column 49 via the line 61. The other part of the liquid collected at the bottom of the column 49 is sent via the line 58 to the column 30.

FIG. 2 schematically shows a method of application of the invention to the treatment of the product resulting from the epoxidation of olefines by the process involving peracids.

The olefine is introduced into the epoxidation reactor 1 via the line 3 and a solution of a percarboxylic acid is introduced via the line 2. The mixture containing the olefine oxide, the carboxylic acid, the solvent and the unconverted olefine is sent via the line 4 into a stripping column 5, from which the greater part of the unconverted olefine is drawn off at the top via the line 6. After partial condensation at 7, the condensed liquid is returned to the column via the line 8, as reflux. The vapours collected via the line 10 are sent into the absorption column 11, where they are absorbed by the solution of percarboxylic acid introduced via the line 12. The volatile components (inert gases) which may be present leave the absorption column via the line 13.

A variant, which is not shown in FIG. 2, consists in absorbing the vapours collected via the line 10, and also, if appropriate, the fresh olefine, in all or part of the solvent collected via the line 40, and in sending the solution thus obtained into the epoxidation reactor 1.

A liquid is collected at the bottom of the stripping column 5 via the line 14 and part of this liquid is sent via the line 15 into the column still 16 before being returned to the distillation column via the line 17. The other part of the liquid collected via the line 14 is sent to the distillation column 19 via the line 18. A liquid is collected at the bottom of the distillation column 19 via the line 25 and part of this liquid is sent to the column still 28 via the line 27 and then to the column 19 via the line 29. The remainder is collected via the line 26; it comprises the carboxylic acid and part of the reaction solvent.

The vapours collected at the top of the column 19 via the line 20 are condensed at 21. Part of the condensate collected at 22 is returned via the line 23 to the column 19, where it provides the reflux, and the other part is sent to the column 30 via the line 24.

The columns 30 and 49 operate in the same manner as in FIG. 1.

The volatile components leaving the condensers 44 and 53 are recovered via the lines 63 and 64, respectively, and are sent to the absorber 11 via the line 10.

In order to illustrate the invention, without thereby restricting the scope thereof, a practical illustrative embodiment is provided below together with an example given by way of comparison.

EXAMPLE 1

This example relates to the purification of a mixture containing propylene oxide, obtained by reacting propylene with perpropionic acid in a medium of 1,2-dichloroethane.

The apparatus is similar to that shown schematically in FIG. 1.

The pressure is 1.1. E+05 Pa in the column 30 and 1.3 E+05 Pa in the column 49. The column 30 is continuously fed via the line 48, at a rate of 1.7 kg/hour, with an aqueous solution containing 5% of sodium hydroxide.

The composition of the product streams in the various parts of the two distillation zones is given in Table 1 below. The feed of product to be distilled is about 100 kg/hour. 33 kg/hour are collected at the top of the column 30. Recycling from the column 49 into the column 30 takes place at a flow rate of 1 liter/hour. The flow rate in the stream 37 is 200 kg/hour.

TABLE 1

|  |  | line 24 | line 38 | line 43 | line 34 | line 62 |
|---|---|---|---|---|---|---|
| propylene, | g/kg | 0.08 | — | 2.53 |  | — |
| ethyl chloride, | g/kg | 0.36 | — | 3.15 |  | — |
| vinyl chloride, | g/kg | 0.02 | 0.01 | 0.5 |  | — |
| dichloroethane, | g/kg | remainder | remainder | — | 6.6 | — |
| water, | g/kg | 11 | 0.33 | 0.04 | remainder | 0.03 |
| acetaldehyde, | g/kg | 0.85 | 0.26 | 1.5 | 0.8 | 0.014 |
| propionaldehyde, | g/kg | 0.35 | 0.00 | 0.00 | 4.8 | — |
| propylene oxide, | g/kg | 292 | 0.02 | remainder |  | remainder |
| methanol, | g/kg | 0.54 | 0.43 | 0.00 | 0.7 | — |
| ethanol, | g/kg | 0.60 | 0.05 | 0.00 | 17 | — |
| acetic acid, | g/kg | 0.40 | 0.00 | 0.06 | 13* | ⎫ |
| propionic acid, | g/kg | 0.98 | 0.00 | 0.00 | 0.2* | ⎬ 0.015 |
| glycol esters, | g/kg | 0.06 | 0.02 | 0.00 |  | — |
| propylene glycol and dimers, | g/kg | 0.04 | 0.36 | <0.01 | 4.3 | — |
| various, | g/kg | 0.12 | 0.38 | 0.20 | 1.1 | — |

*in the form of their sodium salts.

After an operating time of several days, no corrosion is observed in the still of the column 30.

EXAMPLE 2 (comparison)

The same experiment as that in Example 1 was carried out, except that the device enabling the downflow liquid to be collected (the funnel 31) was absent.

In this case, deposits of solids (sodium formate, acetate and the like), which tend to block the thermosiphon reboiler at the bottom of the column, are observed.

The proportion of propylene glycol is very high in this case; a liquid containing from 3 to 6.8 g/kg of propylene glycol is collected via the line 38.

What is claimed is:

1. In a process for the purification of olefine oxides by subjecting a mixture containing the olefine oxide to distillation in a distillation column in the presence of a small amount of water, so as to obtain the olefine oxide as the distillate, the improvement comprises withdrawing a fraction of the liquid flowing down through the column from the column, subjecting the withdrawn fraction to decantation so as to separate off an aqueous phase, which is discarded, and an organic phase, and returning the organic phase to the column at a point located below the withdrawal point.

2. Process according to claim 1, wherein water is introduced into the column in an amount between 0.1 and 20% of the weight of the mixture containing the olefin oxide to be purified entering the column.

3. Process according to claim 1 or 2, wherein the water comprises an aqueous solution of a basic compound which is introduced into the distillation column.

4. Process according to claim 3, wherein an aqueous solution containing from 0.1 to 20% by weight of a basic compound is introduced.

5. Process according to claim 3 wherein the basic compound is selected from the group consisting of alkali metal and alkaline earth metal hydroxides, carbonates, bicarbonates and mixtures thereof.

6. Process according to claim 5, wherein the basic compound is sodium hydroxide.

7. Process according to claim 1 or 2, wherein the mixture containing the olefine oxide to be purified contains from 0.1 to 10% by weight of water and from 0.001 to 5by weight of a compound selected from the group consisting of glycols, esters, aldehydes, alcohols, ketones, carboxylic acids and mixtures thereof, which compounds are by-products from the manufacture of the olefine oxide.

8. Process according to claim 1 or 2, wherein the mixture containing the olefine oxide additionally contains at least one compound selected from the group consisting of the corresponding olefine, solvents, and the carboxylic acids derived from the peracids used to manufacture the olefine oxide.

9. Process according to claim 1 or 2, which is applied to the purification of mixtures containing an olefine oxide selected from the group consisting of propylene oxide, butane oxides, cyclohexene oxide, epichlorohydrin, styrene oxide, diepoxybutane, glycidol and mixtures thereof.

10. Process according to claim 9, which is applied to the purification of mixtures containing propylene oxide.

* * * * *